United States Patent [19]

Blake et al.

[11] 4,427,669

[45] Jan. 24, 1984

[54] CONTRACEPTIVE

[75] Inventors: Charles A. Blake; Jorge F. Rodriguez-Sierra, both of Omaha, Nebr.

[73] Assignee: The Board of Regents of the University of Nebraska, Lincoln, Nebr.

[21] Appl. No.: 392,556

[22] Filed: Jun. 28, 1982

[51] Int. Cl.$^3$ ............................................. A01N 45/00
[52] U.S. Cl. .................................................... 424/238
[58] Field of Search ......................................... 424/238

[56] References Cited

U.S. PATENT DOCUMENTS 3,755,573 8/1973 Berman ................................ 424/238
4,340,602 7/1982 Brooks ................................ 424/238

OTHER PUBLICATIONS

"Steroids" vol. 32, No. 4, Article by Barbieri et al., pp. 529-538.

Primary Examiner—Elbert L. Roberts
Attorney, Agent, or Firm—Vincent L. Carney

[57] ABSTRACT

To prevent pregnancy, female mammals are administered 2-hydroxyestradiol or 4-hydroxyestradiol either before or after ovulation but prior to implantation. The 2-hydroxyestradiol or 4-hydroxyestradiol is mixed with a 0.01% ascorbic acid solution in peanut oil. They are administered either subcutaneously or orally in quantities of at least 0.5 micrograms for every 100 grams of body weight and are administered on at least two consecutive days.

7 Claims, No Drawings

CONTRACEPTIVE

BACKGROUND OF THE INVENTION

This invention relates to contraception.

It is known to use certain steroids, particularly estrogens, as contraceptives for mammals. Estrogens have been used as the postcoital contraceptive of choice for a number of years. Estrogens commonly used have been diethylstilbestrol and ethinylestradiol.

The use of these substances as a postcoital contraceptive has several disadvantages. Numerous clinical laboratories have reported serious side effects on the hepatic and cardiovascular functions. It has also been reported that women treated with diethylstilbestrol have a higher incidence of cervical carcinoma and that their offspring could also be at risk.

The most widely employed steroids for precoital contraception are combinations of synthetic progestogens and synthetic estrogens, their generally being administered during the menstrual period.

The synthetic estrogens in use for precoital contraception also have the disadvantage of certain deleterious side effects in use. Use of these estrogens has been accounted with thromboembolism, increased blood pressure and alterations of the metabolism of lipids and carbohydrates.

SUMMARY OF THE INVENTION

Accordingly, it is an object of the invention to provide a novel method of contraception.

It is a further object of the invention to provide a novel contraceptive method with reduced deleterious side effects compared to current chemical methods of contraception.

It is a still further object of the invention to provide a contraceptive which is a naturally occurring estrogen.

It is a still further object of the invention to provide a contraceptive which has a rapid rate of clearance from blood.

It is a still further object of the invention to provide a contraceptive which can be administered prior to or after ovulation and which operates by preventing implantation of the blastocyst.

It is a still further object of the invention to provide a catecholestrogen as a contraceptive ingredient.

It is a still further object of the invention to provide 2-hydroxyestradiol as a contraceptive.

In accordance with the above and further objects of the invention, a contraceptive is provided, the active ingredient of which is naturally occurring in mammals and has: (1) low estrogenic properties; and (2) a rapid rate of clearance from blood. It is administered either during the first half of the menstrual cycle or prior to implantation during the second half of the menstrual cycle.

For purposes of this description, low estrogenic characteristics means that a sample has a 75 percent or less ability than 17 $\beta$-estradiol ($E_2$) to initiate and maintain the effects induced by $E_2$ which involve the mechanisms for binding to cytosol or nuclear receptors for $E_2$. In the above sentence "initiate and maintain effects" refers to the combined effects of both initiating and maintaining that lead to a single result.

For purposes of this description a rapid rate of clearance from blood relates to a rapid metabolism of a substance in blood compared with that of $E_2$ and thus, a rapid rate of disappearance of a substance from blood compared with that of $E_2$. In the above sentence, "rapid rate" means that the clearance occurs in less than 25 percent of the time required by $E_2$. $E_2$ is the accepted estrogen which is used as a standard for comparison of estrogenic effects with other compounds.

Advantageously the active ingredient is a derivative of estrogen which includes a chemical group that reduces the estrogenic properties of the derivative as compared to $E_2$. More specifically the active ingredient may be a catecholestrogen. It is believed that this material, and particularly 2-hydroxyestradiol, prevents implantation of the blastocyst.

Some catecholestrogens, including 2-hydroxyestradiol, are natural occurring hormones and have been studied in the past by administering them to humans, rats and other mammals. No deleterious side effects have been reported. It has not been known in the past to use this substance as a contraceptive. The use of some catecholestrogens as contraceptives has the advantages of avoiding deleterious side effects present in treatments with other known synthetic estrogens.

SPECIFIC DESCRIPTION

Broadly, contraception in a mammal is provided by reception of the natural estrogen derivative with low estrogenic effect either during the first half of the menstrual cycle or after ovulation but prior to implantation. More specifically, catecholestrogen is administered to rats subcutaneously or orally for at least two days starting on the day of proestrus or starting up to 5 days thereafter. Ovulation normally occurs at about 0400 hours on the day after proestrus (estrus). Implantation of the blastocyst occurs at about 5 days after ovulation.

A specific estrogen is 2-hydroxyestradiol (1,3,5, (10)-estratrien-2, 3,17$\beta$-triol). A related catecholestrogen, 4-hydroxyestradiol, which may not be naturally occurring in some mammals, is also effective. It is possible that compounds may act by one or a combination of the following means: (1) as a catecholamine to block the synthesis of catecholamines by interfering with tyrosine hydroxylase activity and/or to inhibit catechol-o-methyl transferase; (2) as an estrogen or as an anti-estrogen with binding to cytosol estrogen receptors; and (3) as a substance which alters prostaglandin secretion. Alternatively, the compounds may act by some other mechanism.

The contraceptive is prepared by mixing it with a vehicle for convenient administration and to prevent oxidation. Ascorbic acid in oil is satisfactory and a 0.01 percent solution of ascorbic acid in peanut oil (0.1 gram per liter) has been used. The solution may be injected subcutaneously or taken orally. The proper dosage subcutaneously or orally is believed to be at least 0.5 micrograms for each 100 grams of body weight. The proper dosage orally may be greater than the proper dosage subcutaneously due to the susceptibility of steroids to degradation within the gastrointestinal tract and thus the oral dosage to be used will be large enough to compensate for degradation of the contraceptive within the gastrointestinal tract.

A dosage of 5 micrograms of catecholestrogen for each 100 grams of body weight injected subcutaneously is effective and a dosage of 5 micrograms of catecholestrogen for each 1000 grams of body weight injected subcutaneously is not effective on rats using 2-hydroxyestradiol or 4-hydroxyestradiol. A dosage of 50 $\mu$g of catecholestrogen for each 100 grams of body weight administered by gavage is effective on rats using 2-hydroxyestradiol or 4-hydroxyestradiol.

The invention is illustrated by the following examples:

EXAMPLES

The procedure was tested as follows:

GENERAL

Female Sprague-Dawley rats were purchased from Simonsen Laboratories, Inc. (Gilroy, Calif.) and housed in a temperature (24°–26° centigrade)-controlled room with the lights on from 0500 to 1900 hours (h) daily and with rat chow and water available ad libitum. The rats were acclimated to their quarters for two or more weeks before daily vaginal smears by lavage were taken. Rats which exhibited 4- or 5-day estrous cycles were used. The body weight range was 200 to 250 grams. The female rats were placed with a sexually vigorous male of the same strain from 1200 h (noon) proestrus to 1000 h estrus. All female rats had sperm-positive vaginal smears at 1000 h estrus.

DETERMINATION OF OVULATION

Animals were killed by decapitation at 1000 h estrus. The ampulla of each oviduct was removed and placed between two class slides and the number of ova counted with the aid of a stereomicroscope.

DETERMINATION OF PREGNANCY

Animals were killed at 1000 h on the 12th or 13th day after the positive sperm test. The abdominal cavity was opened, the number of fetuses was counted, and the uterus was examined for resorptions.

STEROIDS

All steroids, except estradiol benzoate (EB), were purchased from Steraloids, Inc. (Wilton, N.H.). The EB was a gift from Schering Corporation (Bloomfield, N.J.). The lot numbers for the steroids were: EB (no. 0CX1P16345), 17$\beta$-estradiol ($E_2$, no. 1472), 2-hydroxyestradiol (2-$OHE_2$, no. 2687), estrone ($E_1$, no. 1903), 4-hydroxyestradiol (4-$OHE_2$, no. 2761). The steroids were dissolved in vehicle (peanut oil containing 0.01% ascorbic acid) and injected sc or administered by gavage, always at a volume of 0.1 ml. All steroids purchased from Steraloids, Inc. were found to be greater than 99% pure as determined by using high pressure liquid chromatography.

EFFECTS OF STEROID TREATMENTS FOR 3 DAYS (INITIATED PRIOR TO MATING) ON PREGNANCY

Steroids were administered at 1200 h for 3 days, starting on proestrus (immediately prior to being introduced to the male rat). Pregnancy was determined as described above.

EFFECTS OF STEROID TREATMENTS FOR 1 OR 2 DAYS (INITIATED PRIOR TO MATING) ON PREGNANCY

Steroids were administered at 1200 h for either one or two days, starting on the day of vaginal proestrus. Pregnancy was determined as described above. In addition, other rats were injected with steroids for one day and ovulation was determined as described above.

EFFECTS OF STEROID TREATMENTS FOR 2 DAYS (INITIATED AFTER MATING) ON PREGNANCY

Steroids were administered subcutaneously or by gavage at 1200 h for two days, starting on the day after the sperm positive test (two days after vaginal proestrus) or starting 4, 5, 6 or 7 days after vaginal proestrus.

STATISTICS

The vehicle control groups were compared to groups receiving steroid treatments by the Fisher's exact test.

EXAMPLE I

Steroids were injected subcutaneously in microgram ($\mu$g) doses in oil at 1200 h for 3 days starting on the day of proestrus in 4- or 5-day cyclic rats. Proestrous rats were placed with male rats from 1200 h proestrus until 1000 h estrus. All rats had a positive sperm test at 1000 h estrus and were checked for pregnancy 12 or 13 days later. The results are shown in Table I.

TABLE I

Effects of 3 days of treatment (initiated prior to mating) with 2-hydroxyestradiol (2-$OHE_2$) or estradiol benzoate (EB) on preventing pregnancy in the rat.

| Group | no. pregnant/ no. tested | % pregnant | no. of fetuses[a]/ pregnant rat |
|---|---|---|---|
| Vehicle | 10/11 | 91 | 10.0 ± 0.4 |
| 2-$OHE_2$(500 $\mu$g) | 0/10 | 0** | |
| 2-$OHE_2$(100 $\mu$g) | 0/5 | 0** | |
| 2-$OHE_2$(10 $\mu$g) | 0/4 | 0** | |
| EB (10 $\mu$g) | 0/4 | 0** | |
| 2-$OHE_2$(1 $\mu$g) | 7/8 | 88 | 9.0 ± 1.0 |
| EB (1 $\mu$g) | 2/6 | 33* | (2,4) |

[a]Expressed as mean ±SE or as actual no. of fetuses/individual pregnant rat within parentheses.
*$P < 0.05$ and **$P < 0.01$ when compared to vehicle-treated controls.

RESULTS

All steroid treatments, except the lowest dose of 2—$OHE_2$ (1 $\mu$g) and the lowest dosage of EB (1 $\mu$g), were totally effective in preventing pregnancy in the rats (Table I). The lowest dose of EB (1 $\mu$g) was marginally significant ($P<0.05$) when compared to the vehicle controls. The two rats given the 1 $\mu$g dosage of EB which were pregnant had only 2 and 4 fetuses respectively. There was no evidence of resorption of fetuses in any of these groups or in any of the groups described below.

EXAMPLE II

Steroids were injected subcutaneously in $\mu$g doses in oil at 1200 h for 1 or 2 days starting on the day of proestrus in 4- or 5-day cyclic rats. Proestrous rats were placed with male rats from 1200 h proestrus until 1000 h estrus. All rats had a positive sperm test at 1000 h estrus and were checked for pregnancy 12 or 13 days later. The results are shown in Table II.

TABLE II

Effects of 1 or 2 days of treatment (initiated prior to mating) with 2-hydroxyestradiol (2-$OHE_2$), 4-hydroxyestradiol (4-$OHE_2$), estradiol benzoate (EB), estradiol ($E_2$), or estrone ($E_1$) on preventing pregnancy in the rat.

| Group | no. of days of treatment | number pregnant/ no. tested | % pregnant | no. of fetuses[a]/ pregnant rat |
|---|---|---|---|---|
| 2-$OHE_2$ (500 $\mu$g) | 2 | 0/2 | 0* | |

TABLE II-continued

Effects of 1 or 2 days of treatment (initiated prior to mating) with 2-hydroxyestradiol (2-OHE$_2$), 4-hydroxyestradiol (4-OHE$_2$), estradiol benzoate (EB), estradiol (E$_2$), or estrone (E$_1$) on preventing pregnancy in the rat.

| Group | no. of days of treatment | number pregnant/ no. tested | % pregnant | no. of fetuses[a]/ pregnant rat |
|---|---|---|---|---|
| 2-OHE$_2$ (10 μg) | 2 | 1/5 | 20 | (1) |
| 4-OHE$_2$ (10 μg) | 2 | 0/4 | 0** | |
| EB (10 μg) | 2 | 0/4 | 0** | |
| E$_2$ (10 μg) | 2 | 2/7 | 29* | (1,4) |
| 4-OHE$_2$ (1 μg) | 2 | 4/4 | 100 | 9.0 ± 1.0 |
| EB (1 μg) | 2 | 8/10 | 80 | 5.8 ± 1.5 |
| E$_2$ (1 μg) | 1 | 5/5 | 100 | 7.2 ± 1.8 |
| 2-OHE$_2$ (500 μg) | 1 | 6/6 | 100 | 9.3 ± 1.1 |
| 2-OHE$_2$ (10 μg) | 1 | 5/5 | 100 | 7.8 ± 2.1 |
| EB (10 μg) | 1 | 0/4 | 0** | |
| E$_2$ (10 μg) | 1 | 5/8 | 63 | 10.4 ± 0.2 |
| E$_1$ (100 μg) | 1 | 2/5 | 40 | (10,11) |

*$P < 0.05$ and **$P < 0.01$ when compared to vehicle-treated controls in Table I.
[a]Expressed as mean ±SE or as no. of fetuses/individual pregnant rat within parentheses.

RESULTS

Two days of treatment with 500 or 10 μg of 2—OHE$_2$, 10 μg of 4—OHE$_2$ or 10 μg of EB interfered with the occurrence of pregnancy (Table II). One rat of 5 in the 10 μg 2—OHE$_2$ group had one fetus. Two days of treatment with 10 μg of E$_2$ was partially effective in blocking pregnancy. The two rats given the 10 μg dosage of E$_2$ for two days which were pregnant had only 1 and 4 fetuses respectively. Treatment for one day with 10 μg of EB but not with 10 μg of E$_2$ prevented pregnancy. Treatment for one day with 10 or 500 μg of 2—OHE$_2$ also failed to prevent pregnancy. Treatment with 100 μg of E$_1$ for 1 day did not interfere with the occurrence of pregnancy ($P > 0.05$). The treatments of vehicle or of 10 μg of 2—OHE$_2$, EB, E$_2$ or 4—OHE$_2$ did not prevent ovulation in 4/4, 6/6, 5/5, 4/4 and 4/4 rats respectively.

EXAMPLE III

Steroids in oil were injected subcutaneously or administered by gavage at 1200 h on days 2 and 3 after proestrus (day 0) or on days 4, and 5, 5 and 6, 6 and 7, or 7 and 8 after proestrus in 4- or 5-day cyclic rats. Proestrous rats were placed with male rats from 1200 h proestrus until 1000 h estrus. All rats had a positive sperm test at 1000 h estrus and were checked for pregnancy 12 or 13 days later. The results are shown in Tables III and IV.

TABLE III

Effects of 2 days of treatment (initiated after mating) with 2-hydroxyestradiol (2-OHE$_2$), 4-hydroxyestradiol (4-OHE$_2$), estradiol benzoate (EB), or estradiol (E$_2$) starting 2 days after mating on pregnancy in the rat. Steroids were administered subcutaneously (sc) or by gavage (gv).

| Group | no. pregnant/ no. tested | % pregnant |
|---|---|---|
| Vehicle sc | 6/6 | 100 |
| Vehicle gv | 4/4 | 100 |
| 2-OHE$_2$ (10 μg) sc | 0/6 | 0** |
| 4-OHE$_2$ (10 μg) sc | 0/4 | 0** |
| EB (10 μg) sc | 0/4 | 0** |
| E$_2$ (10 μg) sc | 0/5 | 0** |
| 2-OHE$_2$ (100 μg) gv | 0/5 | 0** |
| 4-OHE$_2$ (100 μg) gv | 0/5 | 0** |

**$P < 0.01$ compared to vehicle-treated controls.

TABLE IV

Effects of 2 days of treatment (initiated after mating) with 2-hydroxyestradiol (2-OHE$_2$) or 4-hydroxyestradiol (4-OHE$_2$) starting 4, 5, 6 or 7 days after mating on pregnancy in the rat. The steroids were administered subcutaneously (sc) or by gavage (gv).

| Group | Injection days after Proestrus | no. pregnant/ no. tested | % pregnant |
|---|---|---|---|
| Vehicle sc | 5,6 | 4/4 | 100 |
| Vehicle sc | 6,7 | 4/4 | 100 |
| Vehicle gv | 5,6 | 4/4 | 100 |
| 2-OHE$_2$ (10 μg) sc | 4,5 | 0/5 | 0** |
| 2-OHE$_2$ (10 μg) sc | 5,6 | 0/5 | 0** |
| 2-OHE$_2$ (10 μg) sc | 6,7 | 5/5 | 100 |
| 2-OHE$_2$ (10 μg) sc | 7,8 | 4/4 | 100 |
| 2-OHE$_2$ (100 μg) gv | 5,6 | 0/5 | 0** |
| 4-OHE$_2$ (10 μg) sc | 5,6 | 0/5 | 0** |
| 4-OHE$_2$ (10 μg) sc | 7,8 | 4/4 | 100 |

**$P < 0.01$ compared to vehicle-treated controls.

RESULTS

Subcutaneous injections of 10 μg of 2—OHE$_2$, 4—OHE$_2$, EB or E$_2$ or the administration of 100 μg of 2—OHE$_2$ or of 4—OHE$_2$ by gavage for 2 days, starting on the second day after vaginal proestrus, prevented pregnancy in all the rats treated (Table III).

Subcutaneous injections of 10 μg of 2—OHE$_2$ for 2 days starting on the fourth or fifth day after vaginal proestrus but not starting on the sixth or seventh day after vaginal proestrus prevented pregnancy in all the rats treated (Table IV). The administration of 100 μg of 2—OHE$_2$ by gavage for 2 days starting on the fifth day after vaginal proestrus prevented pregnancy in all the rats treated (Table IV). Subcutaneous injections of 10 μg of 4—OHE$_2$ for 2 days starting on the fifth day after vaginal proestrus but not starting on the seventh day after vaginal proestrus prevented pregnancy in all the rats treated (Table IV).

Although a preferred embodiment has been described with some particularity, many modifications and variations may be made in the preferred embodiment without deviating from the invention. Accordingly, it is to be understood that, within the scope of the appended claims, the invention may be practiced other than as specifically described.

What is claimed is:

1. A method of contraception of a female mammal comprising the steps of:
   mixing 2-hydroxyestradiol in a vehicle for preventing oxidation of the 2-hydroxyestradiol; and
   administering by subcutaneous injection at least 0.5 micrograms of the 2-hydroxyestradiol to the female for each 100 grams of body weight of the female on at least two consecutive days.

2. A method according to claim 1 in which the step of administering by subcutaneous injection at least 0.5 micrograms of 2-hydroxyestradiol includes the step of administering 0.5 micrograms of 2-hydroxyestradiol for each 100 grams of body weight prior to or within 5 days after ovulation on at least two consecutive days.

3. A method of contraception of a female mammal comprising the steps of:

mixing 2-hydroxyestradiol in a liquid vehicle that prevents oxidation of the hydroxyestradiol to form at least one dose having a rate of clearance from blood sufficiently rapid so that clearance occurs in less than 25 percent of the time required by a sample of the standard 17 β-estradiol, and estrogenicity sufficiently low that a sample has a 75 percent or less ability than 17 β-estradiol to initiate and maintain the effects induced by 17 β-estradiol which involve the mechanisms for binding to cystosol and nuclear receptors for 17 β-estradiol; and administering to the female a dose sufficient to prevent pregnancy while the rate of clearance from blood is rapid.

4. A method according to claim 2 in which the step of administering includes the step of orally administering 2-hydroxyestradiol.

5. A method according to claim 4 in which the step of administering includes the step of administering at least 0.5 micrograms of the 2-hydroxyestradiol for each 100 grams of body weight of the female.

6. A method of contraception of a female mammal comprising the steps of:

mixing 4-hydroxyestradiol in a vehicle for preventing oxidation of the 2-hydroxyestradiol; and administering by subcutaneous injection at least 0.5 micrograms of the 4-hydroxyestradiol to the female for each 100 grams of body weight of the female on at least two consecutive days.

7. A method of contraception of a female mammal comprising the steps of:

mixing 4-hydroxyestradiol in a liquid vehicle that prevents oxidation of the hydroxyestradiol to form at least one dose having a rate of clearance from blood sufficiently rapid so that clearance occurs in less than 25 percent of the time required by a sample of the standard 17 β-estradiol, and estrogenicity sufficiently low that a sample has a 75 percent or less ability than 17 β-estradiol to initiate and maintain the effects induced by 17 β-estradiol which involve the mechanisms for binding to cystosol and nuclear receptors for 17 β-estradiol; and administering to the female a dose sufficient to prevent pregnancy while the rate of clearance from blood is rapid.

* * * * *